US00PP22159P3

(12) United States Plant Patent

Dozier, Jr. et al.

(10) Patent No.: US PP22,159 P3

(45) Date of Patent: Sep. 27, 2011

(54) KIWI PLANT NAMED 'AU GOLDEN SUNSHINE'

(50) Latin Name: ***Actinidia chinensis* Planch**
Varietal Denomination: AU Golden Sunshine

(75) Inventors: William Alfred Dozier, Jr., Opelika, AL (US); Bryan Shelton Wilkins, LaFayette, AL (US); Jim Pitts, Clanton, AL (US); Curtis Jay Hansen, Opelika, AL (US); Floyd M. Woods, Auburn, AL (US); James D. Spiers, Auburn, AL (US); Qinghong Chen, Wuhan (CN); Zhongqi Qin, Wuhan (CN); Yingchun Jiang, Wuhan (CN); Xia Gu, Wuhan (CN); Aichun Xu, Wuhan (CN)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/711,194

(22) Filed: Feb. 23, 2010

(65) Prior Publication Data

US 2011/0209255 P1 Aug. 25, 2011

(51) Int. Cl.
*A01H 5/00* (2006.01)

(52) U.S. Cl. ..... Plt./156

(58) Field of Classification Search ..... Plt./156
See application file for complete search history.

(56) References Cited

OTHER PUBLICATIONS

Wall et al. "Vegetative and Floral Chilling Requirement of Four New Kiwi Cultivars of *Actinidia chinensis* and *A. deliciosa*," (HortScience 43(3):644-647, Jun. 2008.*

Wall et al. "Determining a Maturity Index and the Effect of Chilling Requirements, and Cytokinin Application on Three New Kiwi Cultivars," Thesis—Degree of Master of Science, Auburn University, Aug. 2006, 87 pages.*

* cited by examiner

*Primary Examiner* — Susan McCormick Ewoldt
(74) *Attorney, Agent, or Firm* — Andrus, Sceales, Starke & Sawall, LLP

(57) ABSTRACT

A new and distinct cultivar of the species *Actinidia chinesis* Planch is described. 'AU Golden Sunshine' has a low chilling requirement, fruit is early maturing, excellent flavor with a non acid sweet taste and a high percent solube solids and dry matter content. 'AU Golden Sunshine' matures about 20 days after 'AU Golden Dragon' and 30 days before 'Hort 16A' (patented), the industry standard for golden flesh kiwi cultivars. 'Au Golden Sunshine' fruit quality indices are similar to fruit quality indices of 'AU Golden Dragon' and 'Hort 16A' (patented). There have been no differences in plant performance and fruit quality of 'AU Golden Sunshine' plants grown in China and Alabama.

6 Drawing Sheets

Latin name of the genus and species of the plant claimed: *Actinidia chinensis* Planch.

Variety denomination: 'AU GOLDEN SUNSHINE'.

RELATED APPLICATIONS

U.S. Patent application Ser. No. 12/711,219, filed on Feb. 23, 2010, and entitled "KIWI PLANT NAMED 'AU GOLDEN DRAGON'" and U.S. Patent application Ser. No. 12/711,204, filed on Feb. 23, 2010, and entitled "KIWI PLANT NAMED 'AU GOLDEN TIGER'" are both incorporated by reference herein.

BACKGROUND OF THE INVENTION

'AU Golden Sunshine' is a golden fleshed cultivar of *Actinidia chinensis* Planch. This cultivar was selected from an *Actinidia chinensis* open pollinated seedling orchard that was tended and fruit harvested in Chongyang County of Hubei Province of P.R. China. The parentage of the new cultivar is unknown. 'AU Golden Sunshine' has been asexually reproduced in China and in Alabama, USA by rooting softwood and hardwood cuttings and by whip and cleft grafting. The genetics have been stable through succeeding asexual propagations. 'AU Golden Sunshine' fruit is large, cylindrical and uniform in shape with golden flesh that has a thick sweet flavor and delicious taste. 'AU Golden Sunshine' has high percent soluble solids and dry matter content which does not significantly differ from 'Hort 16A' (U.S. Pat. No. 11,066) (Table 1). 'AU Golden Sunshine' fruit ripens 30 days before 'Hort 16A' (patented), the industry standard for *Actinidia chinensis* cultivars. 'AU Golden Sunshine' fruit contains high levels of health promoting properties.

SUMMARY OF THE INVENTION

The present invention relates to a new and distinct early ripening yellow fleshed kiwi cultivar that produces cylindrical uniform shaped fruit with the stylar end rounded and the stalk end rounded and flat. The fruit skin is brown with short tomentose hairs at maturity.

The new cultivar is able to be asexually reproduced by softwood and hardwood cuttings or by grafting onto a seedling or rooted cutting grown rootstock. The unique characteristics come true to form and are established and transmitted through succeeding asexual propagations. 'AU Golden Sunshine' has been asexually propagated by rooting softwood and hardwood cuttings and by whip and cleft grafting in China and in Alabama, USA.

Kiwi plants are dioecious and have vegetative and compound buds with flower clusters produced in the leaf axils of the first four to six nodes. Male and female flowers are perfect morphologically. The female flower contains some anthers but only the stigma is functional, whereas the flower on a male vine typically produces 125 to 185 large anthers that surround a small, vestigial stigma. In China, Jinxiong 2 (not patented), Kim Woong 3 (not patented), and Kim Woong 4 (not patented) are the male cultivars used as pollenizers. In Alabama 'AU Golden Tiger' is the male cultivar used as the pollenizer for 'AU Golden Sunshine'.

Kiwi buds enter endodormancy during winter, which requires a minimum number of chilling hours for maximum budbreak and bloom. Floral uniformity and density in spring is directly related to the amount of chilling received during winter. It is believed the more accurate measure of chilling hours is Richardson units, which are defined as the accumulated hours between 0° C. and 7° C.

For maximum bud break and flowering of 'AU Golden Sunshine' to occur it was determined that 700 hours of chilling was required and after the chilling requirement was met 15000 growing degree hours were necessary for bud break. The high growing degree hours requirement results in a late bud break and blooming period which occurs after the danger of late spring frost. 'AU Golden Sunshine' has performed well in central Alabama, which has an average winter chilling of 800-1200 hours.

In Alabama, 'AU Golden Sunshine' blooms later in the spring and its fruit ripens earlier in the fall than does 'Hort 16A' (patented). 'AU Golden Sunshine' has a cylindrical fruit shape as does 'Hort 16A' (patented). However, the stylar end is rounded in comparison to protruding stylar end of 'Hort 16A' (patented). The shape of the shoulder on the stalk end of 'AU Golden Sunshine' is rounded to flat in comparison to the rounded shape of 'Hort 16A' (patented). In Alabama, fruit of 'AU Golden Sunshine' matures September 10 in comparison to the fruit of 'Hort 16A' (patented) maturing October 10.

Figure 1:
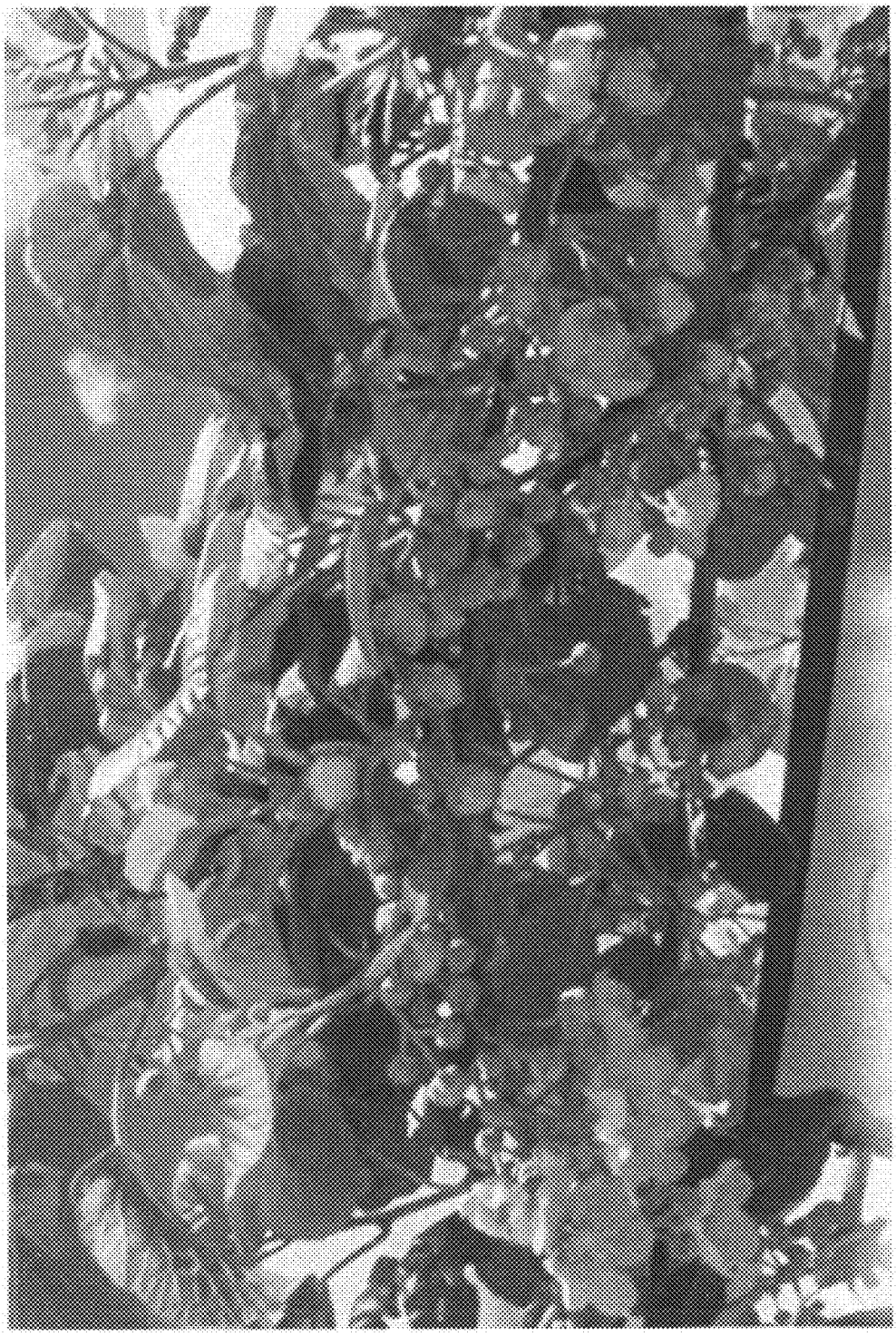
FIG. 1 is a photograph of 'AU Golden Sunshine' flower bud density on 8 year old plants.
Figure 2:
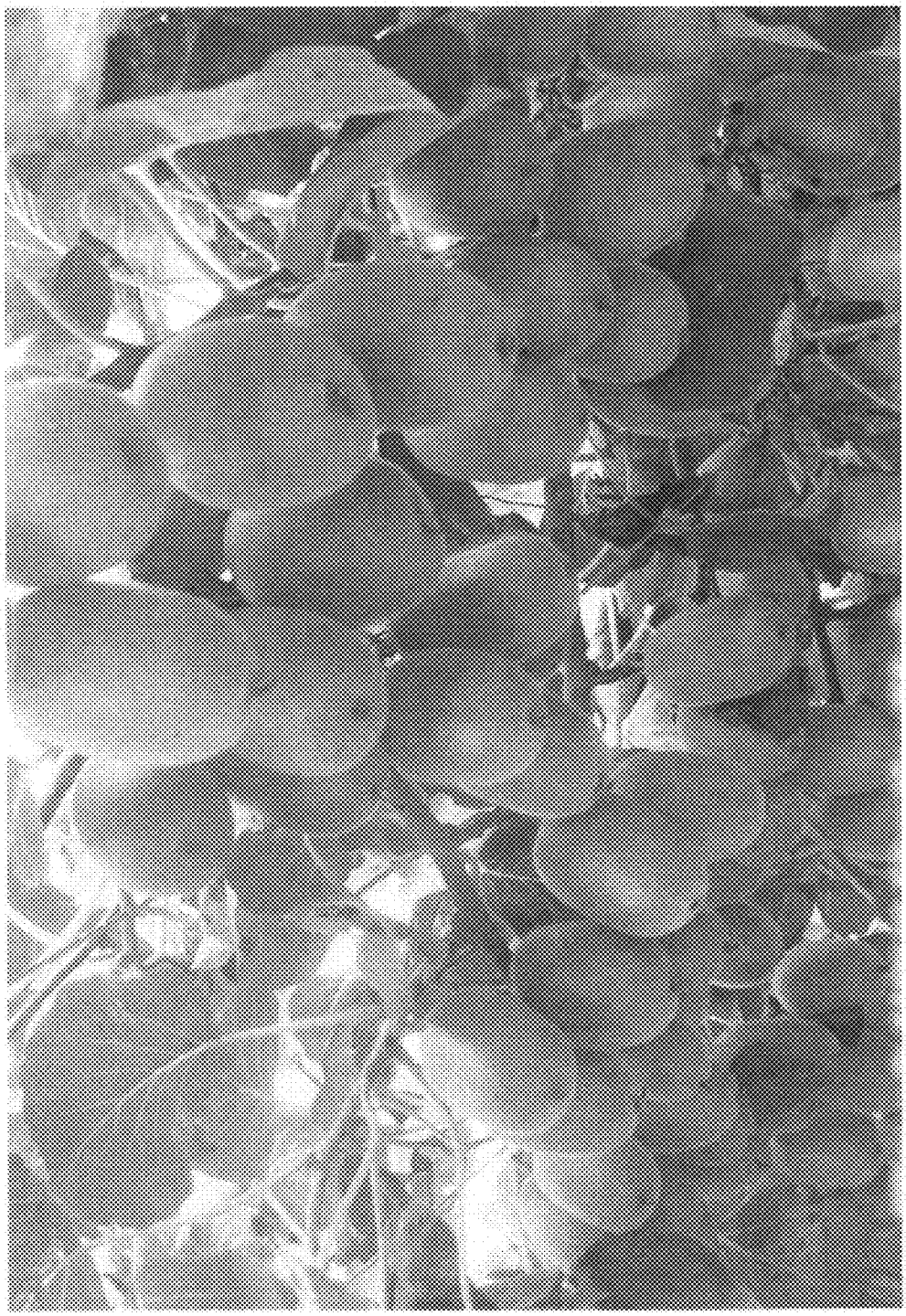
FIG. 2 is a photograph of 'AU Golden Sunshine' close up of fruit on vine on 8 year old plants.
Figure 3:
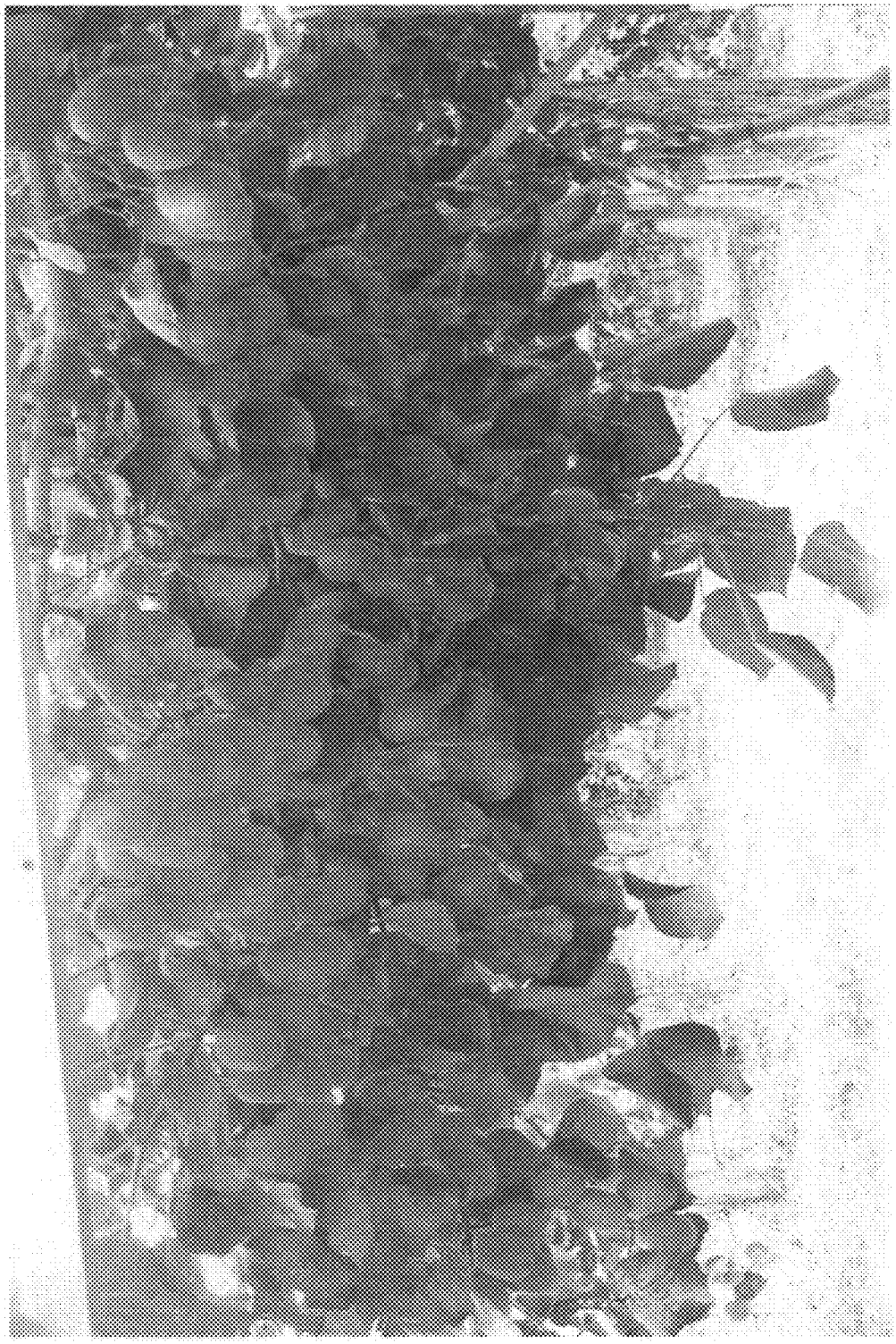
FIG. 3 is a photograph of 'AU Golden Sunshine' fruit load on vine on 8 year old plants.
Figure 4:
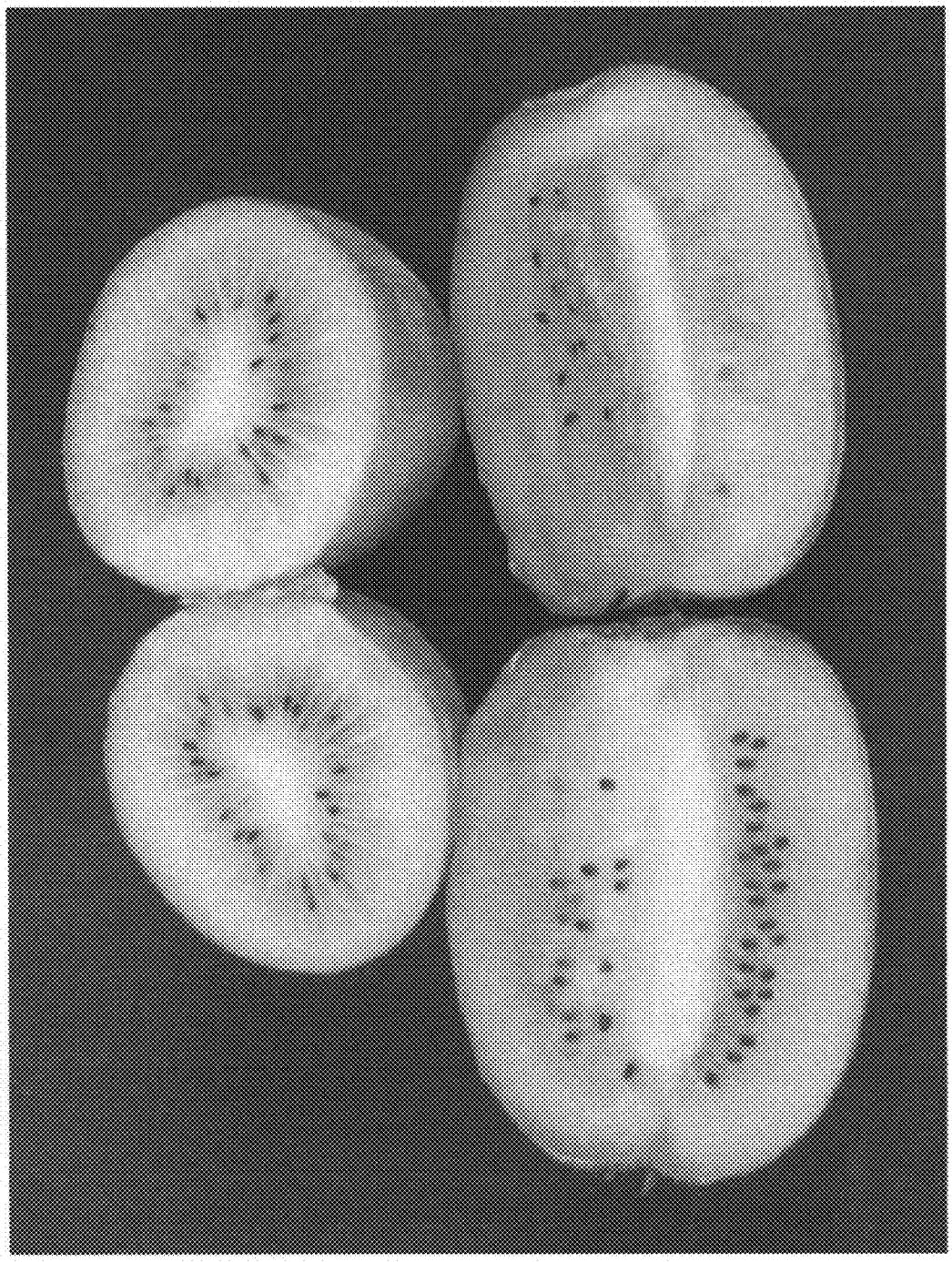
FIG. 4 is a photograph of 'AU Golden Sunshine' flesh color on 8 year old plants.
Figure 5:
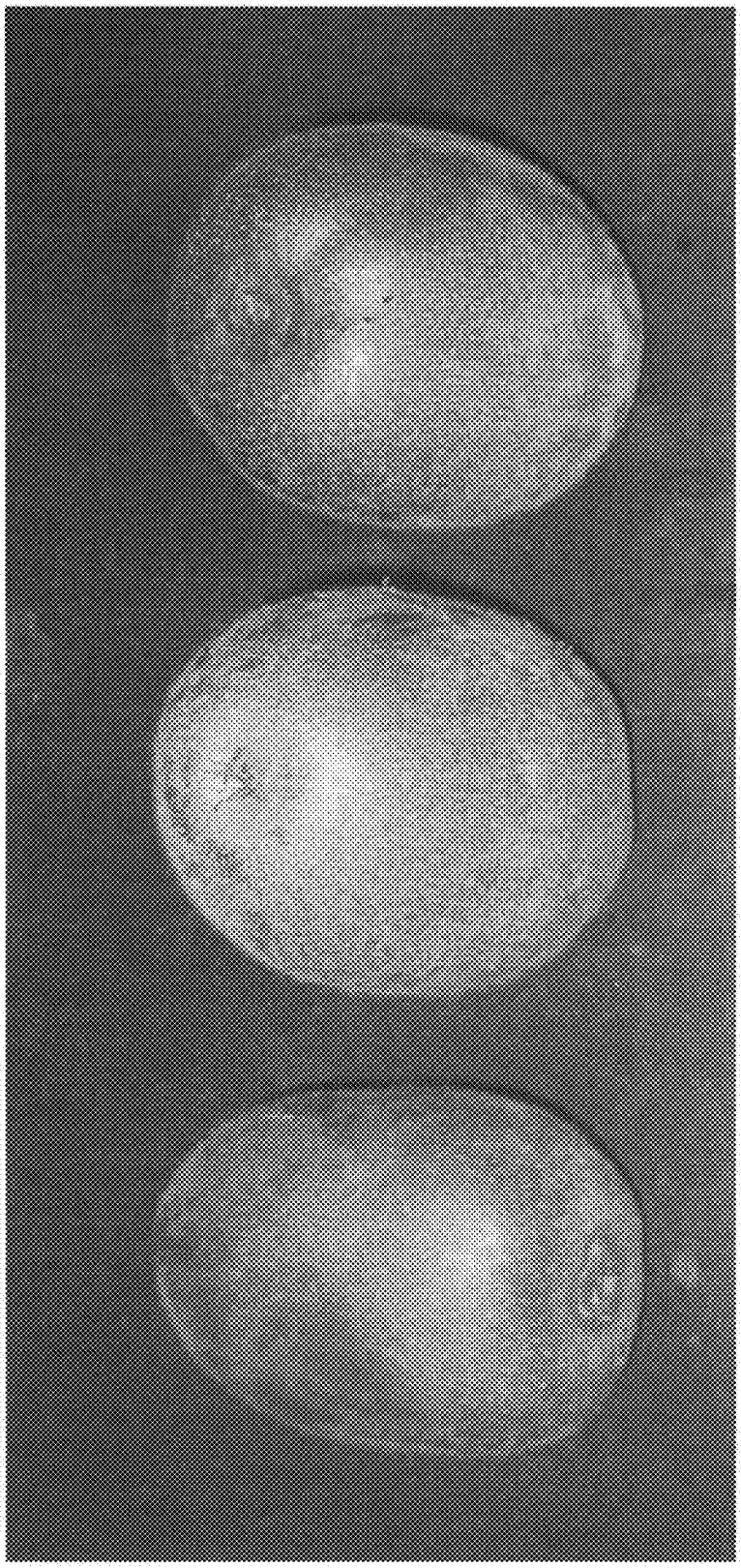
FIG. 5 is a photograph of 'AU Golden Sunshine' fruit shape on 8 year old plants.
Figure 6:
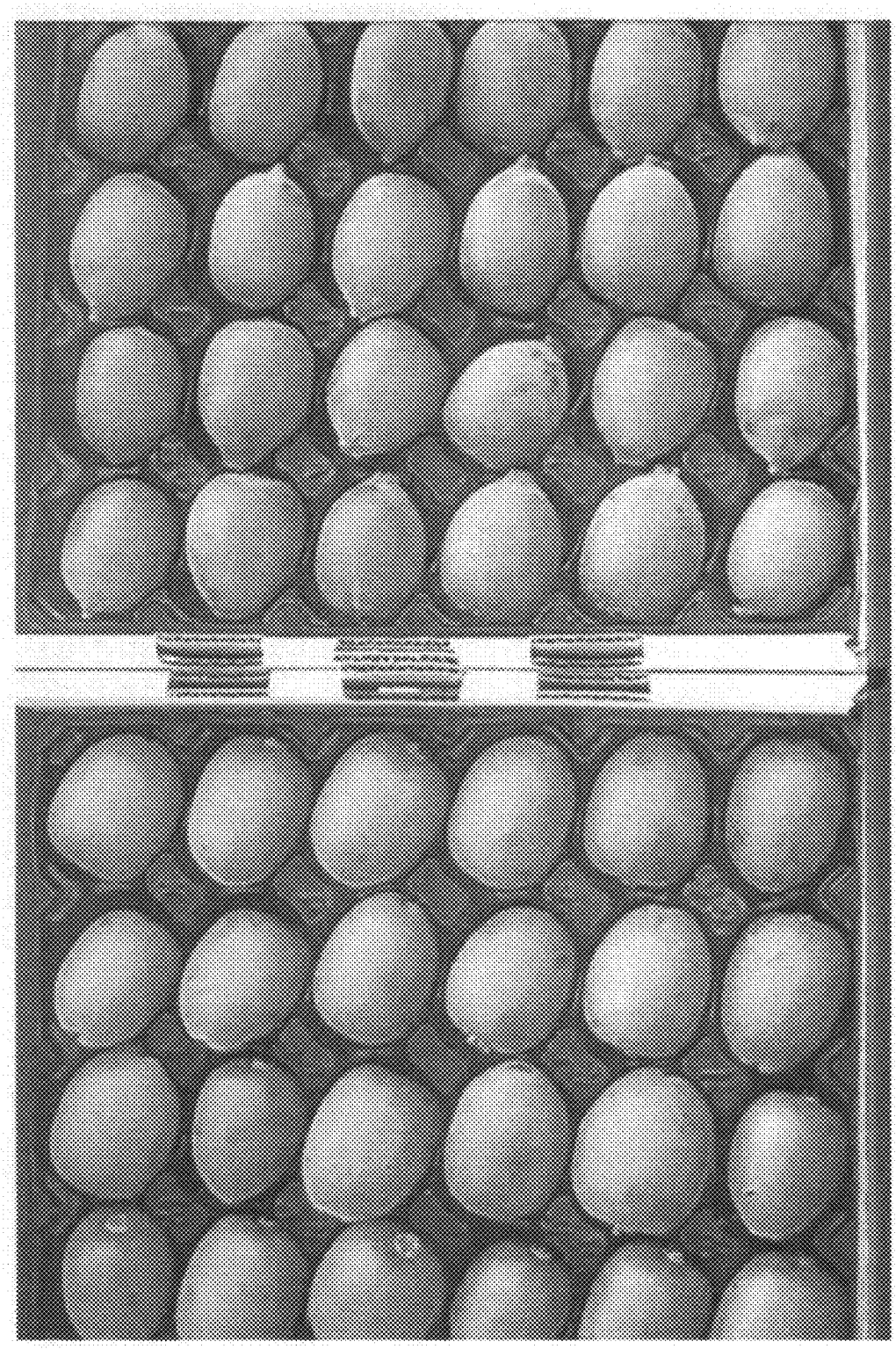
FIG. 6 is a photograph of a comparison of graded and sized fruit of 'AU Golden Sunshine' and 'Hort 16A' on 8 year old plants.

DETAILED BOTANICAL DESCRIPTION:

Kiwi plants are large deciduous shrubs that originated in China and are dioecious, can climb up to 25 feet, and have alternate, broadly rounded petiolate leaves. The cream colored flowers that grow in axillary cymes mature into ovate to oblong fruits (berries) with brownish, hairy skins. There are over 50 species in the genus *Actinidia*. The two *Actinidia* species of the most commercial importance are *deliciosa* and *chinensis*. 'Hort 16A' (patented) is the most important yellow flesh *chinensis* cultivar in the commercial trade. The kiwi plant is dioecious thereby requiring male pollenizers in the presence of the female plants to ensure fruit production. The male and female plants bloom period has to be at the same time for pollination to occur. The bloom period varies with each cultivar depending upon the chilling requirement and the growing degree hour requirement after the chilling requirement has been met. *Actinidia* are temperate zone plants that prefer well drained moist and rich soil and grows as well in a sunny as in a half-shady position.

The new cultivar 'AU Golden Sunshine' is pistillate, with imperfect flowers, e.g. the flowers produce only sterile pollen and thus require a pollenizer for fruit production. The male cultivar 'AU Tiger' is the pollenizer used with 'AU Golden Sunshine'. The bloom period of 'AU Golden Sunshine' starts about April 20 which is 18 days after the 'Hort 16A' (patented) bloom period.

The new cultivar is able to be asexually reproduced by softwood and hardwood cuttings or by grafting or budding onto a seedling or cutting grown rootstock. The unique characteristics come true to form and are established and transmitted through succeeding asexual propagations.

The distinctive characteristics of this new kiwi cultivar described in detail below have been observed in field experiments in Alabama, USA and in China. The 'Hort 16A' (patented) cultivar was evaluated in the same field experiments in Alabama and was used as the standard cultivar for comparison.

The general fruit shape of 'AU Golden Sunshine' is cylindrical, whereas the general shape of 'Hort 16A' (patented) is ovoid. The general shape of the stylar end is rounded on 'AU Golden Sunshine' in comparison to a very protruding stylar end on 'Hort 16A' (patented). The fruit shoulder on the stalk end is rounded and flat on 'AU Golden Sunshine' and rounded on 'Hort 16A' (patented).

'AU Golden Sunshine' blooms with and is pollinized by 'AU Golden Tiger'. 'AU Golden Sunshine' is a companion and comparison fruiting cultivar to 'AU Golden Dragon'. The fruit of 'AU Golden Sunshine' matures 20 days after the fruit of 'AU Golden Dragon' and 30 days before the fruit of 'Hort 16A' (patented). Fruit quality is very similar between the three female cultivars, 'AU Golden Dragon', 'AU Golden Sunshine' and 'Hort 16A' (patented), however they differ in bloom date, fruit maturity date, and fruit shape.

'AU Golden Sunshine' is a good source of health promoting qualities such as vitamin C, antioxidant capacity, β carotene, and total phenolics (Table 2).

Table 3 below illustrates the specific differences between the 'AU Golden Sunshine' cultivar at 8 years of age and the 'Hort 16A' cultivar.

TABLE 3

| | 'AU Golden Sunshine' | 'Hort 16A' (patented) |
|---|---|---|
| Plant | | |
| Plant: sex expression | female (flowers imperfect) | |
| Plant: ploidy | diploid (2n = 2x = 58) | |
| Plant: vigor | strong | |
| Young shoot: hairs | present | |
| Young shoot: density of hairs | medium | |
| Young shoot: type of hairs | short | |
| Young shoot: anthocyanin coloration of growing tip | absent, N199A | |
| Young shoot: anthocyanin coloration of leaf axil | absent, N199A | |
| Plant: average height and spread | plant is a vigorous vine. They are grown on a trellis (either a T-bar or pergola trellis system) in which the plant is | |

TABLE 3-continued

| | 'AU Golden Sunshine' | 'Hort 16A' (patented) |
|---|---|---|
| | allotted a certain space of which it rapidly fills and is maintained in this space by both winter and summer pruning. The trellis is six feet off the ground and the plant is allowed each summer to grow and hang down on each side of the trellis. | |
| **Stem** | | |
| Stem: coloration of leaf axil | absent, N199A | |
| Stem: diameter | medium | medium |
| Stem base diameter | mean 12.9 mm (range 10-18.1 mm) | mean 11.0 mm (range 8.3-13.3 mm) |
| Stem mid section diameter | mean 9.7 mm (range 7.4-12.5 mm) | not available |
| Stem: dormant bud diameter | 4.2 mm (2.5-6.1 mm) | 6.9 mm (4.9-8.3 mm) |
| Stem: color on upper side of shoot | grey-brown, N199A | dark brown, 200B-200C-165A |
| Stem: character of bark | smooth | |
| Stem: hairs | few | present |
| Stem: conspicuousness of lenticels | weak | conspicuous |
| Stem: number of lenticels | few | medium |
| Stem: color of lenticels | brownish-white, 199C | |
| Stem: size of bud support | large | |
| Stem: visibility of bud (dormant canes) | visible | |
| Stem: number of hairs visible on bud (dormant canes) | high | medium |
| Stem: leaf scar | mean length 5.5 mm (4.7-5.9 mm) mean width 5.7 mm (5-6.3 mm) | medium |
| **Leaf (Mature)** | | |
| Leaf shape: | broadly cordate to orbicular | very broadly ovate |
| Leaf base shape: | rounded to cordate; lobes not overlapping | cordate |
| Leaf tip shape: | broadly obtuse with cuspidate tip | cuspidate |
| Leaf margin: | entire | ciliate |
| Leaf adaxial surface: | medium to dark green; glabrous except for sparse, unbranched hairs along veins, 147A | light-medium green, medium glossiness, 146A |
| Leaf abaxial surface: | light green; dense, stellate pubescence everywhere except along main veins which are densely tomentose with unbranched hairs, 147B | light green, 147B |
| Leaf length (cm): | 20.1 (16.8-24.1) | 17 (14.5-19.8) |
| Leaf width (cm): | 15.3 (13.1-18.2) | 18.6 (15.9-21.7) |
| Leaf ratio (l/w): | 1.3 (1.2-1.5) | |
| Leaf petiole length (cm): | 6.4 (5-8.7) | 16.7 (10-25) |
| Leaf 1° vein organization: | pinnate; veins terminating as small extended points or mucros at leaf margins | |
| Leaf 2° vein organization: | parallel | |
| Leaf puckering: | weak | |
| Leaf variegation: | none | |
| Leaf spines on lower leaf surface: | none; dense stellate hairs | |
| Petiole: | 147C | |
| Pedicel: | N199A | |

TABLE 3-continued

| | 'AU Golden Sunshine' | 'Hort 16A' (patented) |
|---|---|---|
| **Flower** | | |
| Inflorescence#: predominate number flower buds/stem | mean 2.2 (range 1-3) | mean 1.0 |
| 1° Pedicel length (cm): | 3.7 (2.5-4.6) | 4.2 (3.0-4.9) |
| 2° Pedicel length (cm): | 1.8 (1.4-2.1) | |
| Pedicel pubescence: | minutely, densely tomentose, unbranched | |
| Sepalf#: | 5.7 (5-8) | >5 |
| Sepal color: | greyed-green to slightly rust colored at margin, 191C | |
| Sepal pubescence: | minutely, densely tomentose, unbranched | |
| Flower color: | creamy white, 155D | White, 155D |
| Flower width (cm): | 5.0 (4.8-5.8) | 1.8 (1.6-1.9) |
| Petal orientation: | distinct to overlapping | overlapping |
| Petal #: | 6.4 (5-9) | 8 (6-10) |
| Petal length (cm): | 2.1 (1.7-2.5) | 2.3 (2.1-2.5) |
| Petal width (cm): | 1.6 (1.4-2.1) | 1.8 (1.6-1.9) |
| Petal ratio (l/w): | 1.3 (1.0-1.6) | 1.3 (1.1-1.5) |
| Ovary shape: | globose | |
| Ovary pubescence: | minutely, densely pilose; unbranched | strongly expressed |
| Style#: | 20 (17-22) | 30.85 (26 - 36) |
| Style orientation: | upright to spreading | erect |
| Stamen#: | 85.4 (80-96) | |
| Anther length (mm): | 3.0-4.0 | |
| Filament: | 155D | |
| Anther: | 169D | |
| Chilling requirement hours: | 700 | |
| **Fruit** | | |
| Fruit: average weight (g) | 90.4 (47.7-149.6) | 98.3 (43-176) |
| Fruit: length (mm) | 66.8 (51.9-80.3) | 79.1 (76.0-84.2) |
| Fruit: width (max) (mm) | 48.4 (38.4-62.8) | 53.1 (55.4-48.1) |
| Fruit: L/A ratio (max width) | 1.38 | 1.49 |
| Fruit: width (min) (mm) | 44.7 (37.3-51.8) | 49.1 (47.0-51.2) |
| Fruit: L/D ratio (min width) | 1.49 | 1.61 |
| Fruit: core diameter (max) (mm) | 14.3 (3.2-21.7) | 13.1 (9.1-17) |
| Fruit: core diameter (min) (mm) | 5.6 (2.7-12.7) | 4.9 (4.1-6.1) |
| Fruit: locule number | 36.8 (31-40) | 34.5 (26-37) |
| Fruit: peduncle length (mm) | 28.7 (21.6-34.2) | 48.3 (44.7-50.3) |
| Fruit: peduncle width (mm) | 1.7 (1.2-2.6) | 3.57 (3.2-4.3) |
| Fruit: general shape | cylindrical | ovoid |
| Fruit: cross-section at median | round | elliptic |
| Fruit: general shape of stylar end | rounded | |
| Fruit: shape of shoulder on stalk end | rounded, flat | rounded |
| Fruit: skin color at harvest | Brown, N199A | yellow-brown |
| Fruit: skin color change during ripening | absent | yellow-brown |
| Fruit: skin color at maturity for consumption | brown, N199A | combination of 199A plus 161A |
| Fruit: hairs | present | medium |
| Fruit: density of hairs | light | pubescent |
| Fruit: types of hairs | tomentose | |
| Fruit: hair length (mm) | short (0.05-0.15) | |
| Fruit: concentration of hairs | uniform | |

TABLE 3-continued

| | 'AU Golden Sunshine' | 'Hort 16A' (patented) |
|---|---|---|
| Fruit: adherence of hairs to skin (when rubbed) | weak | |
| Fruit: core diameter (at largest diameter) | large (10.0 mm by 3.4 mm) | small |
| Fruit: core shape (in cross section) | elliptical | |
| Fruit: core woody spike | present | |
| Fruit: prominence of core woody spike | medium | weak |
| Fruit: outer pericarp color at maturity for consumption | yellow green, 152C-152D | golden yellow, 12C-12B |
| Fruit: inner pericarp color (locules) at maturity for consumption | yellow green, 148A | brownish-yellow, 162A-162C |
| Fruit: core color at maturity | greyed-yellow, 160C | white, 159C |
| Fruit: seed color at maturity in flesh | dark brown, 200A | 200A |
| Fruit: seed color when dry | greyed-orange, 165B | Brown, 200D |

Notes regarding Table 3:

1. Horticulture terminology is used in accordance with revised UPOV guidelines for kiwi.
2. Characters of comparison cultivar 'Hort 16A' are noted opposite that character when significantly different.
3. 'Hort 16A' plants were observed in the same experimental planting as the new cultivar.
4. All dimensions are in millimeters unless otherwise stated; weights are in grams.
5. The RHS 1966 color chart used to determine actual color.

TABLE 1

Fruit Quality at harvest and after 30 days cold storage treatment of three *Actinidia chinensis* Planch golden kiwi cultivars grown in central Alabama and China.

| | Harvest[z] | | | |
|---|---|---|---|---|
| Cultivar | Firmness (Kg) | Soluble Solids (%) | Dry Matter (%) | Internal Hue Angle |
| 'AU Golden Dragon' | 4.4b[y] | 6.6c | 17.2 | 104 |
| 'AU Golden Sunshine' | 4.7b | 8.6b | 18.5 | 100 |
| 'Hort 16A' (patented) | 5.8a | 11.7a | 21.0 | 105 |

TABLE 1-continued

Fruit Quality at harvest and after 30 days cold storage treatment of three *Actinidia chinensis* Planch golden kiwi cultivars grown in central Alabama and China.

| | 30 Days Cold Storage[x] | | | |
|---|---|---|---|---|
| Cultivar | Firmness (Kg) | Soluble Solids (%) | Dry Matter (%) | Internal Hue Angle |
| 'AU Golden Dragon' | 1.1 | 15.2 | 18.0 | 99 |
| 'AU Golden Sunshine' | 0.0 | 15.7 | 18.5 | 94 |
| 'Hort 16A' (patented) | 2.0 | 17.4 | 21.0 | 101 |

[z]Means derived from data taken in the 2006, 2008, 2009 and 2010 growing seasons. There was not fruit in 2007 due to a late spring frost killing flower buds.
[y]Mean separation within columns by Duncan's Multiple Range Test p = 0.05, columns without letters were not significantly different.
[x]Means derived from data taken in 2003, 2004, 2008, 2009 and 2010 for 'Au Golden Dragon' and 'AU Golden Sunshine" and in 2009 and 2010 for 'Hort 16A' (patented).

TABLE 2

Phytochemical properties of 'AU Golden Dragon' and 'AU Golden Sunshine' cultivars.

| Phytochemical properties | 'AU Golden Dragon' | 'AU Golden Sunshine' |
|---|---|---|
| Ascorbic acid (mg/100 g FW) | 96.98 | 94.43 |
| Vitamin C equivalent Antioxidant capacity (VCEA) | 161.60 | 177.90 |
| B carotene (mg/100 g FW) | 0.20 | 0.23 |
| Chlorophyll a (mg/100 g FW) | 0.11 | 0.12 |
| Chlorophyll b (mg/100 g FW) | 0.06 | 0.05 |
| Total Phenolics (mg GAE/100 g FW) | 135.70 | 155.50 |

What is claimed is:

1. A new and distinct variety of *Actinidia chinensis* Planch plant named 'AU Golden Sunshine' substantially as described and illustrated herein.

* * * * *